(12) United States Patent
Bowens-Jones et al.

(10) Patent No.: US 7,404,946 B2
(45) Date of Patent: Jul. 29, 2008

(54) ANTIPERSPIRANT METHODS AND COMPOSITIONS

(75) Inventors: Andrea Demetrius Bowens-Jones, Cincinnati, OH (US); Antoinette Lynn Allen, Liberty Township, OH (US)

(73) Assignee: The Procter and Gamble Company, Cincinnati, OH (US)

( * ) Notice: Subject to any disclaimer, the term of this patent is extended or adjusted under 35 U.S.C. 154(b) by 919 days.

(21) Appl. No.: 10/719,755

(22) Filed: Nov. 21, 2003

(65) Prior Publication Data

US 2005/0112073 A1  May 26, 2005

(51) Int. Cl.
*A61Q 15/00* (2006.01)
*A61K 8/02* (2006.01)

(52) U.S. Cl. .......................... 424/65; 424/401
(58) Field of Classification Search ................ 424/65, 424/401
See application file for complete search history.

(56) References Cited

U.S. PATENT DOCUMENTS

| | | |
|---|---|---|
| 4,963,591 A | 10/1990 | Fourman et al. |
| 5,508,024 A | 4/1996 | Tranner |
| 5,593,663 A | 1/1997 | Leng et al. |
| 5,700,455 A | 12/1997 | Hinterwaldner et al. |
| 5,869,600 A | 2/1999 | Causton et al. |
| 5,948,882 A | 9/1999 | Causton et al. |
| 6,149,897 A * | 11/2000 | Swaile .................... 424/65 |
| 6,274,127 B1 | 8/2001 | Schraer et al. |
| 6,387,356 B1 | 5/2002 | Csernica et al. |
| 2002/0001572 A1 | 1/2002 | Brewster |
| 2003/0194387 A1 | 10/2003 | Murphy |

FOREIGN PATENT DOCUMENTS

| | | |
|---|---|---|
| GB | 1192021 A | 5/1970 |
| WO | WO 9324105 A | 12/1993 |
| WO | WO 9744010 A | 11/1997 |

* cited by examiner

*Primary Examiner*—Sreeni Padmanabhan
*Assistant Examiner*—Renee Claytor
(74) *Attorney, Agent, or Firm*—Andrew J. Hagerty; Brian M. Bolam; Tara M. Rosnell

(57) ABSTRACT

An antiperspirant compositions and corresponding methods of application wherein the compositions comprise a) a skin-adhering system comprising i) a skin-adhering polymer, ii) one or more volatile solvents; b) antiperspirant active; c) thickening agent; and d) an anhydrous carrier in an amount sufficient to provide enhanced substantivity of antiperspirant actives.

15 Claims, No Drawings

US 7,404,946 B2

ANTIPERSPIRANT METHODS AND COMPOSITIONS

FIELD OF THE INVENTION

The present invention relates to antiperspirant compositions and corresponding methods of application wherein the compositions comprise skin-adhering polymers for enhanced substantivity of antiperspirant actives.

BACKGROUND OF THE INVENTION

Many topical antiperspirant products are commercially available in a variety of formulations and product forms. These products typically contain a solid and/or liquid carrier in combination with an antiperspirant active. Antiperspirant actives help to reduce or eliminate perspiration on the underarm or other areas of the skin. It is believed that these antiperspirant actives work by dissolving in sweat after application, diffusing as a dissolved material into the sweat ducts, and then precipitating in the sweat ducts to form a plug that inhibits the flow of perspiration. Although the antiperspirant actives are capable of providing this function, the actives are not able to achieve optimum performance due to their inability to adhere to the skin. After application, most of the actives flake off or are transferred from the skin onto clothing or other material thereby leaving only a minimal amount of active available to inhibit the flow of perspiration.

The present invention provides alternative antiperspirant compositions to those that are currently available or otherwise known in the art. The present invention also provides such alternative compositions through the use and application of skin adhering polymers contained by or within a suitable volatile anhydrous carrier. Further, the present invention provides such alternative compositions with improved antiperspirant efficacy.

SUMMARY OF THE INVENTION

The present invention provides an antiperspirant with novel compositions that allow for retention of actives on the skin in order to alleviate or prevent the flow of perspiration. These compositions comprise a skin-adhering system comprising skin adhering-polymers and one or more volatile solvents. The skin-adhering polymer in combination with the volatile solvent form a system that works to retain the antiperspirant actives on the skin thereby improving the efficacy of the actives to prevent or inhibit sweat. The present invention is also directed to methods for inhibiting or preventing perspiration by topically applying to the underarm or other appropriate area of skin a composition comprising a skin-adhering system as described herein, in addition to antiperspirant actives, thickening agents and an anhydrous carrier.

It has been found that the topical antiperspirant compositions and methods of application as disclosed herein provide alternative antiperspirant formulations and methods from those commercially available or otherwise known. It has also been found that these compositions and applied methods provide improved antiperspirant efficacy and/or cosmetics as compared to many other more traditional antiperspirant products.

DETAILED DESCRIPTION OF THE INVENTION

The antiperspirant compositions and methods of the present invention can comprise, consist essentially of, or consist of, the essential components as well as optional ingredients described herein. As used herein, "consisting essentially of" means that the composition or component may include additional ingredients, but only if the additional ingredients do not materially alter the basic and novel characteristics of the claimed compositions or methods.

All percentages, parts and ratios are based upon the total weight of the topical compositions of the present invention and all measurements made are at 25° C., unless otherwise specified. All such weights as they pertain to listed ingredients are based on the active level and, therefore, do not include carriers or by-products that may be included in commercially available materials, unless otherwise specified.

The term "anhydrous" as used herein, unless otherwise specified, refers to those materials or compositions that are substantially free of added water. As it pertains to the compositions of the present invention, this means that the compositions are essentially free of added water. The term "anhydrous", however, as used herein can also mean that the composition contains water but that the water is isolated. The term "anhydrous" as used herein generally means that the material or composition preferably contains less than 1%, preferably less than 0.5%, more preferably zero percent, by weight of free or added water.

The term "antiperspirant efficacy" as used herein, unless otherwise specified, refers to any incremental sweat reduction resulting from an antiperspirant composition as a result of the addition of the skin-adhering polymer and volatile anhydrous carrier described herein. Sweat reduction is determined by the hot room procedure described in U.S. Pat. No. 6,352,688, Scavone, issue date Mar. 5, 2002.

The term "skin-adhering polymer" as used herein, unless otherwise specified, refers to those polymers that when applied to skin form flexible substantive films. These materials function as substantivity aids to trap or hold the active onto the skin for a time sufficient to provide the desired efficacy benefit. In the case of antiperspirants, the polymer maintains adhesion to skin through multiple sweat events, thus the antiperspirant active is available longer thereby providing the advantageous efficacy benefit.

The term "volatile solvent" of the present invention refers to solvents that exhibit vapor pressures of at least about 0.10, preferably at least about 1.00 and no more than about 10.00, preferably no more than about 100.00 (mmHg) at about 20° C.

The term "skin-adhering system" as used herein refers to the combination of one or more skin-adhering polymers and one or more volatile solvents. The skin-adhering polymer in combination with the volatile solvent form a system that works to retain the antiperspirant actives on the skin thereby improving the efficacy of the actives to prevent or inhibit sweat.

"Sufficient film-formation" as used herein describes the ability of the skin-adhering polymer to form a cohesive film.

The term "ambient conditions" as used herein, refers to surrounding conditions at about one atmosphere of pressure (1 atm), at about 50% relative humidity, unless otherwise specified. All values, amounts and measurements described herein are obtained under ambient conditions unless otherwise specified.

The essential elements of the antiperspirant compositions of the present invention, including the essential elements of the corresponding methods of application, are described in greater detail hereinafter.

Skin-Adhering Polymers

The antiperspirant compositions of the present invention comprise skin-adhering polymers. By being skin-adhering polymers, the polymers suitable for use in the present invention readily adhere to and form films on skin, thereby depositing the active incorporated with the polymers in the composition onto the skin. The polymers may be completely soluble or dispersible in the anhydrous carrier. Polymers of the present invention include, but are not limited to, acrylate polymers/co-polymers and silicone polymers/co-polymers. Examples of acrylate co-polymers include, but are not limited to, various combinations of acrylate and/or methacrylate monomers, including acrylic-ester and acrylic-acid monomers. Examples of silicone-modified co-polymers include, but are not limited to, silicone-acrylate copolymers, silicone-urethane copolymers, silicone-maleic anhydride copolymers, silicone resin copolymers, and mixtures thereof.

The skin-adhering polymers suitable for use in the compositions and methods of the present invention will generally have a relatively low glass transition temperature (Tg). In order to prevent or minimize flaking on the skin, it is suitable for the Tg to be within a range that allows flexibility of the polymer. Thus, it is preferred that compositions of the present invention include a Tg from at least about −30° C., more preferably at least about 0° C., even more preferably at least about 3° C. The Tg of the present invention should be no more than about 30° C., more preferably no more than about 20° C., even more preferably no more than about 10° C.

It is preferred that the skin-adhering polymers of the present invention exhibit a number average molecular weight that allows for sufficient film-formation to the skin. Useful skin-adhering polymers of the present invention exhibit sufficient film-formation at or above the entanglement molecular weight according to the polymer used. For example, when a silicone-acrylate copolymer is used in compositions of the present invention, the molecular weight is at or about 400,000 g/mol number average for sufficient film-formation.

The concentration of the skin-adhering polymers in the composition should be sufficient to provide the desired antiperspirant efficacy when used in combination with conventional antiperspirant actives. Applicants of the present invention have found that the skin-adhering polymer will typically range from at least about 0.1%, preferably from at least about 2%, more preferably from at least about 3%, even more preferably from at least about 4% to no more than about 30%, preferably no more than about 20%, more preferably no more than about 15%, even more preferably no more than about 10%, by weight of the composition. Polymers of the present invention should be included such that a suitable amount of polymer attaches to the skin without inhibiting release of the antiperspirant active ingredients and without aesthetic tradeoffs. Thus, a ratio of weight compositions of polymer to thickening agent should be considered such that the weight composition of polymer is directly proportional to the weight composition of thickening agent. The ratio of weight compositions of polymer to thickening agent (in semi-solid form) suitable for the present invention should include the weight composition of polymer to be no more than about 2, preferably no more than about 1.5, more preferably no more than about 1, even more preferably no more than about 0.64, still more preferably no more than about 0.5 directly proportional to the weight composition of thickening agent which, is at least about 1.

Volatile Solvent

The antiperspirant compositions of the present invention also comprise volatile solvents. Suitable volatile solvents exhibit vapor pressures of at least about 0.10, preferably at least about 1.00 and no more than about 10.00, preferably no more than about 100.00 (mmHg) at about 20° C. The function of the volatile solvent as part of the skin-adhering system is to aid in rapid film formation by evaporating quickly on skin to leave behind the polymer film, active, and other components. This prevents product transfer prior to dry down. In addition, by evaporating rapidly, the volatile solvent leaves physical channels in the dried polymer/antiperspirant film. This aids in rapid dissolution of the active in the dried polymer/antiperspirant film during a sweat event. Volatile solvents of the present invention include, but are not limited to, alcohols, silicone fluids, fluorinated solvents and mixtures thereof. Alcohols of the present invention may include polar, nonpolar, organic, non-organic carriers and mixtures thereof that are known for use in antiperspirant/deodorant or other personal care products, or which are otherwise suitable for topical applications to skin. Particularly preferred alcohols include ethanol, propanol, isopropanol and mixtures thereof. The concentration of the volatile solvents of the present invention will typically range from at least about 0.1%, preferably from at least about 2%, more preferably from at least about 3%, even more preferably from at least about 5% to no more than about 60%, preferably no more than about 50%, more preferably no more than about 40%, even more preferably no more than about 30%, by weight of the composition.

Antiperspirant Actives

Antiperspirant actives suitable for use in the compositions of the present invention include any compound, composition or other material having antiperspirant activity. Preferred actives comprise astringent metallic salts, especially the inorganic salts of aluminum zirconium and zinc, as well as mixtures thereof. Particularly preferred are the aluminum and zirconium salts, such as aluminum halides, aluminum chlorohydrate, aluminum hydroxyhalides, zirconyl oxyhalides, zirconyl hydroxyhalides, and mixtures thereof.

Preferred aluminum salts for use in the composition include those that conform to the formula:

$$Al_2(OH)_aCl_b \cdot xH_2O$$

wherein a is from about 2 to about 5; the sum of a and b is about 6; x is from about 1 to about 6; and wherein a, b, and x may have non-integer values. Particularly preferred are the aluminum chlorohydroxides referred to as "5/6 basic chlorohydroxide", wherein a=5, and "2/3 basic chlorohydroxide", wherein a=4. Processes for preparing aluminum salts are disclosed in U.S. Pat. No. 3,887,692, Gilman, issued Jun. 3, 1975; U.S. Pat. No. 3,904,741, Jones et al., issued Sep. 9, 1975; U.S. Pat. No. 4,359,456, Gosling et al., issued Nov. 16, 1982; and British Patent Specification 2,048,229, Fitzgerald et al., published Dec. 10 1980. Mixtures of aluminum salts are described in British Patent Specification 1,347,950, shin et al., published Feb. 27, 1974.

Preferred zirconium salts for use in the composition include those that conform to the formula:

$$ZrO(OH)_{2-a}Cl_a \cdot xH_2O$$

Wherein a is from about 1.1 to about 2.0; x is from about 1 to about 8; and wherein a and x may both have non-integer values. These zirconium salts are described in Belgian Patent 825,146, Schmitz, issued Aug. 4, 1975, which description is incorporated herein by reference. Particularly preferred zirconium salts are those complexes that additionally contain aluminum and glycine, commonly know as ZAG complexes. These ZAG complexes contain aluminum chlorohydroxide and zirconyl hydroxy chloride conforming to the above described formulas. Such ZAG complexes are described in U.S. Pat. No. 3,679,068, Luedders et al., issued Feb. 12, 1974;

Great Britain Patent Application 2,144,992, Callaghan et al., published Mar. 20, 1985; and U.S. Pat. No. 4,120,94, Shelton, issued Oct. 17, 1978.

The concentration of the antiperspirant actives of the present invention will typically range from at least about 0.1%, preferably from at least about 2%, more preferably from at least about 3%, even more preferably from at least about 5% to no more than about 30%, preferably no more than about 27%, more preferably no more than about 25%, even more preferably no more than about 20%, by weight of the composition.

Thickening Agent

The antiperspirant compositions of the present invention also comprise thickening agents to help provide the composition with the desired viscosity, rheology, texture and/or product hardness, or to otherwise help suspend any dispersed solids or liquids within the composition. The term "thickening agent" includes any material known or otherwise effective in providing suspending, gelling, viscosifying, solidifying or thickening properties to the composition or which otherwise provide structure to the final product form. These thickening agents include gelling agents, and polymeric or nonpolymeric or inorganic thickening or viscosifying agents. The thickening agents will most typically include organic solids, silicone solids, crystalline or other gellants, inorganic particulates such as clays or silicas, or combinations thereof.

The concentration and type of the thickening agent selected for use in the antiperspirant composition will vary depending upon the desired product form, viscosity, and hardness. Most thickening agents suitable for use herein, will have a concentration range from at least about 0.1%, more preferably from at least about 3%, even more preferably from at least about 5% to no more than about 35%, more preferably no more than about 20%, even more preferably no more than about 10%, by weight of the composition.

Non limiting examples of suitable gelling agents of the present invention include fatty acid gellants, salts of fatty acids, hydroxyl acids, hydroxyl acid gellants, esters and amides of fatty acid or hydroxyl fatty acid gellants, cholesterolic materials, dibenzylidene alditols, lanolinolic materials, fatty alcohols, triglycerides, sucrose esters such as SEFA behenate, inorganic materials such as clays or silicas, other amide or polyamide gellants, and mixtures thereof. Concentrations of all such gelling agents are preferably from at least about 0.1%, more preferably from at least about 1%, even more preferably from at least about 5% and no more than about 25%, more preferably no more than about 15%, even more preferably no more than about 10%, by weight of the composition.

Suitable gelling agents include fatty acid gellants such as fatty acid and hydroxyl or alpha hydroxyl fatty acids, having from about 10 to about 40 carbon atoms, and ester and amides of such gelling agents. Non-limiting examples such gelling agents include 12-hydroxystearic acid, 12-hydroxylauric acid, 16-hydroxyhexadecanoic acid, behenic acid, eurcic acid, stearic acid, caprylic acid, lauric acid, isostearic acid, and combinations thereof. Preferred are 12-hydroxystearic acid, esters of 12-hydroxystearic acid, amides of 12-hydroxystearic acid and combinations thereof.

Other suitable gelling agents include amide gellants such as disubstituted or branched monoamide gellants, monsubstituted or branched diamide gellants, triamide gellants, and combinations thereof, including n-acyl amino acid derivatives such as n-acyl amino acid amides, n-acyl amino acid esters prepared from glutamic acid, lysine, glutamine, aspartic acid, and combinations thereof. Other suitable amide gelling agents are described in U.S. Pat. No. 5,429,816, issued Jul. 4, 1995, and U.S. patent application Ser. No. 08/771,183, filed Dec. 20, 1996.

Still other examples of suitable gelling agents include fatty alcohols having at least from about 8 carbon atoms, preferably from at least about 12 carbon atoms and no more than about 40 carbon atoms, preferably no more than about 30 carbon atoms, more preferably no more than about 18 carbon atoms. Preferred fatty alcohols, but are not limited to cetyl alcohol, myristyl alcohol, stearyl alcohol and combinations thereof, more preferably stearyl alcohol.

Non limiting examples of suitable tryiglyceride gellants include tristearin, hydrogenated vegetable oil, trihydroxysterin (Thixcin® R, available from Rheox, Inc.), rape seed oil, castor wax, fish oils, tripalmitin, Syncrowax® HRC and Syncrowax® HGL-C (Syncrowax® available from Croda, Inc.).

Other suitable thickening agents include waxes or wax-like materials having a melt point of above 65° C., more typically from about 65° C. to about 130° C., examples of which include, but are not limited to, waxes such as beeswax, carnauba, bayberry, candelilla, montan, ozokerite, ceresin, hydrogenated castor oil (castor wax), synthetic waxes and microcrystalline waxes. Castor wax is preferred within this group. Other high melting point waxes are described in U.S. Pat. No. 4,049,792, Elsnau, issued Sep. 20, 1977.

Further thickening agents for use in the antiperspirant compositions of the present invention include inorganic particulate thickening agents such as clays and colloidal pyrogenic silica pigments. Preferably, colloidal pyrogenic silica pigments are used. One common example includes Cab-O-Sil®, a submicroscopic particulated pyrogenic silica. Other known or otherwise effective inorganic particulate thickening agents that are commonly used in the art can also be used in the antiperspirant compositions of the present invention. Concentrations of particulate thickening agents preferably range from at least about 0.1%, more preferably from at least about 1%, even more preferably from at least about 5% to no more than about 15%, more preferably no more than about 10%, even more preferably no more than about 8%, by weight of the composition.

Suitable clay thickening agents include montmorillonite clays, examples of which include bentonites, hectorites, and colloidal magnesium aluminum silicates. These and other suitable clays are preferably hydrophobically treated, and when so treated will generally be used in combination with a clay activator. Non-limiting examples of suitable clay activators include propylene carbonate, ethanol, and combinations thereof. When clay activators are present, the amount of clay activator will typically range from at least about 40%, more preferably from at least about 25%, even more preferably from at least about 15% to no more than about 75%, more preferably no more than about 60%, even more preferably no more than about 50%, by weight of the clay.

Anhydrous Carrier

The antiperspirant compositions of the present invention also comprise anhydrous carriers. Anhydrous carriers of the present invention include, but are not limited to silicone fluids. The silicone fluid is preferably a cyclic silicone, more preferably a cyclic silicone having from at least about 3 silicone atoms, even more preferably at least about 5 silicone atoms but no more than about 7 silicone atoms, more preferably no more than about 6 silicone atoms.

The concentration of the anhydrous carrier useful in the present invention will typically range from at least about 10%, preferably from at least about 15%, more preferably from at least about 20%, even more preferably from at least about 25% to no more than about 70%, preferably no more than about 65%, more preferably no more than about 60%, even more preferably no more than about 50%, by weight of the composition.

Optional Materials

The antiperspirant compositions of the present invention may further comprise other optional materials known for use in antiperspirant, deodorant or other personal care products, including those materials that are known to be suitable for topical application to skin. Non limiting examples include dyes or colorants, fragrances, emulsifiers, distributing agents, pharmaceuticals or other topical actives, deodorant agents, antimicrobials, preservatives, surfactants, processing aides such as viscosity modifiers and wash-off aids. Examples of such optional materials are described in U.S. Pat. No. 4,049, 792 (Elsnau); U.S. Pat. No. 5,019,375 (Ianner et al.) and U.S. Pat. No. 5,429,816 (Hofrichter et al.).

Product Form

The antiperspirant compositions of the present invention can be formulated as any known or otherwise effective product form for providing topical application of antiperspirant or deodorant active to the desired area of the skin. Non-limiting examples of such product forms include liquids (e.g., aerosols, pump sprays, roll-ons), solids (e.g., gel solids, invisible solids, wax solid sticks), semi-solids (e.g. creams, soft solids, lotions), and the like. Preferably, the antiperspirant compositions of the present invention are semi-solids or solids.

The antiperspirant products are generally stored in and dispensed from a suitable package or applicator device, such as a cream dispenser with perforated application domes, etc. These packages should be sufficiently closed to prevent excessive loss of volatiles prior to application.

Method of Manufacture

The antiperspirant compositions of the present invention may be prepared by any known or otherwise effective technique, suitable for providing an anhydrous composition of the desired form and having the essential materials described herein. Many such techniques are described in the antiperspirant/deodorant formulation arts for the described product forms.

Method of Use

The antiperspirant compositions of the present invention may be applied topically to the underarm or other suitable area of the skin in an amount effective to reduce or inhibit perspiration wetness. Preferably, compositions of the present invention is applied in an amount ranging from at least about 0.1 gram to no more than about 20 grams, preferably no more than about 10 grams, more preferably no more than about 1 gram. The composition is preferably applied to the underarm at least about one or two times daily, preferably once daily, to achieve effective antiperspirant reduction or inhibition over an extended period.

The antiperspirant composition can also be applied every other day, or every third or fourth day, and then optionally to supplement application on off-days with other personal care products such as deodorants and/or conventional antiperspirant formulations.

Compositions of the present invention are preferably applied to skin, wherein the volatile anhydrous carrier leaves behind a skin-adhering polymer and active-containing film. This film is positioned over the sweat ducts and resists flaking and/or rub-off, thereby being present through multiple perspiration episodes.

EXAMPLES

The composition described in Table 1 is an antiperspirant composition in the form of a semi-solid (cream). This exemplified composition can be prepared by methods well known in the art for creams, some examples of which are described in U.S. Pat. No. 6,187,300 (Motely et al.).

All exemplified amounts are weight percentages based on the total weight of the antiperspirant composition, unless otherwise specified. Examples of the present invention are not intended to be limiting thereof:

TABLE 1

Semi-solid (Cream) Antiperspirant Stick

| Ingredients | Weight (%) |
|---|---|
| Al Zr trichlorohydrex[1] | 25.25 |
| Isopropanol | 43.5 |
| Cyclomethicone, D5[2] | 15.0 |
| Dimethicone (10 cs) | 5.0 |
| C20–C40 alcohols[3] | 5.0 |
| Skin-Adhering Polymer | 4.0 |
| C18–36 triglyceride combination | 1.25 |
| Fragrance | 1.0 |

[1]Supplied by Westwood Chemical Corporation
[2]Cyclic polydimethylsiloxane containing 5 carbons, supplied by G.E. Silicones
[3]Syncrowax HGL-C from Croda The composition described in Table 2 is an antiperspirant composition in the form of a solid stick. This exemplified composition can be prepared by methods well known in the art for preparing such product forms, examples of such methods including those described in U.S. Pat. No. 4,985,238 (Tanner et al.).

TABLE 2

Solid Antiperspirant Stick

| Ingredients | Weight (%) |
|---|---|
| Al Zr trichlorohydrex | 20.0 |
| Stearyl Alcohol | 12.0 |
| Cyclomethicone, D5 | 50.0 |
| Talc | 10.0 |
| Skin-Adhering Polymer | 3.0 |
| Hydrogenated castor oil | 3.0 |
| Fragrance | 1.0 |
| Silica | 0.4 |
| Microthene | 0.4 |
| Behenyl Alcohol | 0.2 |

The compositions described in Table 3 are antiperspirant compositions in the form of roll-on liquids and aerosols. Each of these exemplified compositions can be prepared by methods well known in the art for preparing such product, forms, examples of such methods including those described in U.S. Pat. No. 4,904,463 (Johnson et al.) and U.S. Pat. No. 5,298, 236 (Orr et al.).

TABLE 3

Liquid Antiperspirant Roll-Ons and Aerosols

| Ingredients | Weight (%) (Roll-On) | Weight (%) (Aerosol) |
|---|---|---|
| Skin-Adhering Polymer | 3.0 | 4.0 |
| Cyclohexasiloxane | 40.3 | 12.4 |
| Dimethiconol 80 cs | 10.0 | — |

TABLE 3-continued

Liquid Antiperspirant Roll-Ons and Aerosols

| Ingredients | Weight (%) (Roll-On) | Weight (%) (Aerosol) |
| --- | --- | --- |
| Dimethicone 50 cs | — | 5.0 |
| Mineral Oil | 10.0 | — |
| Al Zr trichlorohydrex gly. | 25.0 | — |
| Quaternium-18 Hectorite HL | 4.0 | 1.0 |
| Propylene Carbonate | 1.0 | 0.3 |
| Dipropylene glycol | 0.9 | — |
| Polyethylene powder | 5.5 | — |
| Al chlorohydrate | — | 12.0 |
| Propellant | — | 60.0 |
| Isopropyl myristate | — | 5.0 |
| Perfume | 0.3 | 0.3 |

The antiperspirant composition described in Table 4 is in the form of an emulsion. This exemplified composition can be prepared by methods well known in the art for emulsions, some examples of which are described in U.S. Pat. No. 4,673,570 (Soldati).

TABLE 4

Antiperspirant Emulsion

| Ingredients | Weight (%) |
| --- | --- |
| Al Zr trichlorohydrex glycinate | 20.0 |
| Skin-Adhering Polymer | 4.0 |
| Cyclohexasiloxane | 6.0 |
| Cyclomethicone (and) dimethicone copolyol DC 3225C | 15.0 |
| PPG-15 Stearyl Ether | 9.0 |
| Perfume | 1.0 |
| Water | 45.0 |

All documents cited in the Detailed Description of the Invention are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. Anhydrous, antiperspirant compositions comprising:
   a. a skin-adhering system comprising:
      i) a skin-adhering polymer;
      ii) one or more volatile solvents;
   b. antiperspirant active;
   c. thickening agent selected from the group consisting of organic solids, silicone solids, gellants. inorganic particulates, and mixtures thereof; and
   d. an anhydrous carrier in an amount sufficient to provide antiperspirant efficacy and wherein the skin-adhering polymer and thickening agent are different.

2. The composition of claim 1 wherein the composition comprises
   a. a skin-adhering system comprising:
      i) from about 0.1% to about 30%, by weight, of a skin-adhering polymer;
      ii) from about 0.1 to about 60%, by weight, of one or more volatile solvents;
   b. from about 0.1 to about 30%, by weight, of an antiperspirant active;
   c. from about 0.1 to about 35%, by weight, of a thickening agent; and
   d. from about 10% to about 70%, by weight, of an anhydrous carrier.

3. The composition of claim 1 wherein the skin-adhering polymer is selected from the group consisting of acrylate polymers/co-polymers, silicone polymers/co-polymers, and mixtures thereof.

4. The composition of claim 3 wherein the acrylate polymer/co-polymer comprises monomers selected from the group consisting of acrylate monomers, methacrylate monomers, and mixtures thereof.

5. The composition of claim 3 wherein the silicone polymer/co-polymer comprises copolymers selected from the group consisting of silicone-acrylate copolymers, silicone-urethane copolymers, silicone-maleic anhydride copolymers, silicone resin copolymers, and mixtures thereof.

6. The composition of claim 1 wherein the skin-adhering polymer has a glass transition temperature (Tg) of from at least about −30° C. to about 30° C.

7. The composition of claim 1 wherein the skin-adhering polymer exhibits film-formation at or above the entanglement molecular weight of the polymer used.

8. Anhydrous, antiperspirant compositions comprising:
   a a skin-adhering system comprising:
      i) a skin-adhering polymer;
      ii) one or more volatile solvents;
   b antiperspirant active;
   c thickening agent; and
   d an anhydrous carrier in an amount sufficient to provide antiperspirant efficacy, wherein the ratio of the weight percentage of polymer to the weight percentage of the thickening agent is from about 2:1 to about 0.5:1.

9. The composition of claim 1 wherein the volatile solvent is selected from the group consisting of alcohols, silicone fluids, fluorinated solvents, and mixtures thereof.

10. The composition of claim 9 wherein the alcohol is selected from the group consisting of ethanol, propanol, isopropanol, and mixtures thereof.

11. The composition of claim 1 wherein the antiperspirant active is selected from the group consisting of zirconium salts, aluminum salts, and mixtures thereof.

12. The composition of claim 1 wherein the anhydrous carrier is a cyclic silicone fluid having from at least about 3 silicone atoms to about 7 silicone atoms.

13. The composition of claim 1 further comprising a pharmaceutical.

14. The composition of claim 1 further comprising a deodorant agent.

15. The composition of claim 1 further comprising an antimicrobial.

* * * * *